United States Patent [19]

Ribeiro et al.

[11] Patent Number: 4,834,804

[45] Date of Patent: May 30, 1989

[54] PROCESS FOR THE PRESERVATION AND CLEANING OF HYDROPHILIC LENSES

[76] Inventors: Antonio C. H. Ribeiro, Rua Guaianazes, 91, Sao Francisco, Niteroi-RJ 24250, Brazil; David Gryner, Rua Prudente de Morais, 1022, Apt. 801, Ipanema, Rio de Janeiro, Brazil, 22420; Antonio P. Capella, Rua General Espirito Santo Cardoso, No. 576, Tijuca, Rio de Janeiro 20530, Brazil

[21] Appl. No.: 779,781

[22] PCT Filed: Jan. 9, 1985

[86] PCT No.: PCT/BR85/00001

§ 371 Date: Sep. 6, 1985

§ 102(e) Date: Sep. 6, 1985

[87] PCT Pub. No.: WO85/03018

PCT Pub. Date: Jul. 18, 1985

[30] Foreign Application Priority Data

Jan. 9, 1984 [BR] Brazil .................... PI8400090[U]

[51] Int. Cl.$^4$ .............................................. B08B 3/10
[52] U.S. Cl. .......................................... 134/4; 134/17; 134/42; 422/28
[58] Field of Search ................. 134/4, 17, 42; 422/28

[56] References Cited

U.S. PATENT DOCUMENTS

| | | | |
|---|---|---|---|
| 2,854,360 | 9/1958 | Pajes | 134/17 X |
| 3,419,427 | 12/1968 | Plock | 134/17 X |
| 3,908,680 | 9/1975 | Krezanoski | 134/27 |
| 3,948,679 | 4/1976 | Lewis | 134/17 X |
| 4,409,034 | 10/1983 | Williams | 134/17 X |
| 4,490,389 | 12/1984 | Nelson et al. | 422/28 X |
| 4,491,484 | 1/1985 | Williams | 134/4 |
| 4,560,491 | 12/1985 | Sherman | 422/28 X |
| 4,585,488 | 4/1986 | Giefer | 134/42 X |

*Primary Examiner*—Asok Pal
*Attorney, Agent, or Firm*—Shlesinger & Myers

[57] ABSTRACT

A method for removing organic and inorganic deposits from hydrophilic (contact) lenses and minimizing shape deformation thereof, comprising immersing the lenses in an aqueous solution of water and a hypertonic, substantially nontoxic cryoscopic modifying agent, reducing the temperature of the solution to between 0° C. and −4° C., thereby causing the solution to freeze and expand and causing the lens structure to contract, and causing the liquid volume to exceed the lens hydrogel volume and expelling deposits in the lens and on the lens surface.

2 Claims, No Drawings

PROCESS FOR THE PRESERVATION AND CLEANING OF HYDROPHILIC LENSES

TECHNICAL FIELD

This invention relates to the preservation and cleaning of lenses in general and, more particularly to a process for the preservation and cleaning of hydrophilic lenses by means of the freezing in hypertonic solution of sodium chloride or another substance that modifies the cryoscopic solution degree.

BACKGROUND OF THE INVENTION

As known in the field with which the present invention is related to, one of the topics of greatest controversy in contactology is undoubtedly the theme related to the preservation of hydrophilic lenses.

As known, there are two available processes for the treatment of hydrophilic lenses, i. e., the chemical and the thermal.

Asepsis and preservation chemical process uses basically thimerosalt and, as a preservative, the chloroxedine. The advantages relative to this process are related to its efficiency as an antisseptic and to its handling facility. The high cost of the products, however, the development of hypersensitiveness processes with consequent intolerance to the use of lenses and the greatest facility of inorganic impregnation with, for instance, mercury and calcium salts, arise as negative factors limiting its utilization.

Three different stages may be outstanding in this process, thus included: lenses cleaning after use, with an available product, for example, PLIAGEL; preservation with products based on thimerosalt and chloroxedine; disproteinization periodically, with the purpose of making the proteins lysine, having as active agent, the papain. Among the three stages, the disproteinization may be considered the one that presents the best results, inside what it proposes.

However, the thermic process is constituted by two different technics, which are: The hot (by boiling) and the cold (by freezing).

The preservation process by heat is the most used and consists on the direct boiling or in water-bath, in a saline solution or distilled water. Apparently, boiling only presents the advantage of making calcium salts, in the form of carbonate, more soluble, which make difficult its impregnation and difficultates lipids deposition. This process, however, sins by the great risk of damn made to the lenses when realized under direct boiling in a common oven, what does not occur with electric aseptizers. Boiling also promotes the protein cooking, making them more agglutinated and adherent to the villosities of lens surface. We may cite as an example the phenomenon occurring with the white of the egg, basically constituted by albumine, a protein that predominates in the human tear, which on being subjected to cooking, gets firm and opaque, therefore different enough from its initial state. In the case of lenses, proteins also have these transformations and are therefore much more adherent and difficult to be removed when exposed to disproteinization. Boiling also promotes the shortening of the average lenses life, so as to increment polymeric instability.

DISCLOSURE OF THE INVENTION

The present invention has the object of solving these problems providing a process for the preservation of hydrophilic lenses by freezing cold, a process that is simple, of low operational cost and developing no toxity at all.

Taking into consideration the problems found out with the precedent processes, the inventor of the present process discovered that on submitting hydrophilic lenses to freezing, the latter presented neatly cleaner, what has been demonstrated and proved in a practical and theoretical form.

Exhaustive studies and tests have demonstrated that hydrophilic lenses subjected to the process of this invention allow, not only to diminish the secretion, but to increment also in a sensible way, the usuary comfort, of lenses subjected to the freezing process. Another advantage, verified in the use of this process is that the risk of damage, compared to the preceding processes, is equal to zero, since the lenses support freezing for an indefinite time.

Another advantageous aspect of the process in the present invention is that the toxicity is nill, since we only use a sodium chloride solution in a concentration which is about 5.0% to 0.09% or another substance that modifies the solution cryoscopic degree, preferently without the preservatives. The operational cost is also practically nill since the lenses freezing is obtained through a conventional house refrigerator.

The following are some physical and chemical aspects of the process advantages according to this invention.

DESCRIPTION OF THE PREFERRED EMBODIMENT

As known, the fat depositions are those which impregnate more rapidly the hydrophilic lenses surface. Some experiments have demonstrated that after 30 minutes use, 50% of the lenses area are already involved with fat depositions. On submitting lenses to freezing, it was verified that these depositions are taken away owing to the fat agglutination mechanism. The most common example which may be offered, in an illustrative sense, is that observed when we put a fat food into a refrigerator. As the food is heated or hot, fat takes away and gets more fluid, spreading all over the container surface where it is. As food is put into the refrigerator, it is verified that after some time the fat of that food condensates in a uniform way and in a same level. This is exactly the phenomenon occurring on the lenses, by the fact that fats agglutinate at a molecular level at the moment they are refrigerated, as a great puzzle was mounted. On the other hand, as that fat is heated, the molecular interaction force is undone as the puzzle were dismounted.

Once the agglutination phenomenon occurred, it was decided to research the reason why this material was taken away and this stage was classified as a "unglueing phenomenon", coming to the following conclusion:

Considering that hydrophilic lenses present a structure somewhat similar to the sponges - in the passage from liquid to solid state, it is observed that:

(1) gelatinous material contracts itself, i. e., it diminishes its volume;

(2) liquid contained in gelatinous material expands itself;

once the liquid volume is larger than hidrogel volume, its expulsion occurs, carrying along with it all the components spread on lens surface. For this reason, the organic depositions find it dificult to fix on lenses treated by means of process of the present invention.

For inorganic depositions, principally calcium salts the, pumping mechanism by contraction due to cold, also makes its impregnation difficult.

The contamination by fungi and bacteria becomes significantly lower. As bacteria depend on the deposition of mucus to develop themselves and also by the very action of cold, they do not contrive do adhere the lenses surface.

Finally, polymeric stability of hydrophilic lenses, subjected to the process of the invention is superior to that of lenses subjected to the other conventional processes of preservation, what enlarges hydrophilic lenses over life.

I claim:

1. A method of removing organic and inorganic deposits caused by wear of a hydrophilic lens and minimizing shape deformity thereof, comprising the steps of:

removing the lens from the eye where the lens has organic and inorganic deposits within and on the lens surface, immersing the lens in an aqueous solution of water and a hypertonic, substantially nontoxic cryoscopic modifying agent, reducing the temperature of the solution to between 0° C. to −4° C. thereby causing the solution to freeze and expand and causing the lens structure to contract, causing the liquid volume to exceed the lens hydrogel volume and expelling deposits contained in the lens and deposits located on the lens surface.

2. The method of claim 1 where the cryroscopic modifying agent is sodium chloride.

* * * * *